United States Patent [19]

Jokela

[11] Patent Number: 4,837,685
[45] Date of Patent: Jun. 6, 1989

[54] ANALOG PREPROCESSOR FOR JAW TRACKING DEVICE

[75] Inventor: Richard E. Jokela, Puyallup, Wash.

[73] Assignee: Myo-Tronics Research, Inc., Seattle, Wash.

[21] Appl. No.: 16,020

[22] Filed: Feb. 18, 1987

[51] Int. Cl.⁴ ............................................. G06F 15/42
[52] U.S. Cl. ............................... 364/413.02; 128/777; 433/69
[58] Field of Search ........... 128/777; 364/415, 413.02; 433/69

[56] References Cited

U.S. PATENT DOCUMENTS

| | | |
|---|---|---|
| 3,822,694 | 7/1974 | Mills . |
| 4,197,855 | 4/1980 | Lewin ................. 128/653 |
| 4,303,077 | 12/1981 | Lewin et al. . |
| 4,342,086 | 7/1982 | Adib . |
| 4,383,535 | 5/1983 | Schorr . |
| 4,386,405 | 5/1983 | Lewin et al. ............ 364/415 |
| 4,386,614 | 6/1983 | Ryan . |
| 4,447,207 | 5/1984 | Kataoka ................. 128/777 |
| 4,459,109 | 7/1984 | Radke . |

FOREIGN PATENT DOCUMENTS

| | | | |
|---|---|---|---|
| 84108496.5 | of 0000 | European Pat. Off. . | |
| 2936328 | 3/1981 | Fed. Rep. of Germany ...... 128/777 |
| 3002267 | 7/1981 | Fed. Rep. of Germany ...... 128/777 |
| 3136674 | 4/1983 | Fed. Rep. of Germany ...... 128/777 |

Primary Examiner—Joseph Ruggiero
Assistant Examiner—Gail O. Hayes
Attorney, Agent, or Firm—Christensen, O'Connor, Johnson & Kindness

[57] ABSTRACT

An improved analog preprocessor for a jaw tracking device having a plurality of magnetic sensors (44), each of which produces a first analog signal corresponding to the position of a magnet fixed with respect to the patient's mandible. The preprocessor includes analog means (200) for electrically combining the first analog signals to produce at least one analog position signal representing the position of the magnet along one axis, a gain select circuit (302) for providing a gain select signal, a variable slope ramp generator that provides a ramp signal having a slope corresponding to the gain select signal, a comparator for comparing the position and ramp signals and generating an output pulse having a length corresponding to the magnitude of the position signal, and a low pass filter for receiving the output pulse and producing an analog movement signal having a magnitude corresponding to the pulse length.

5 Claims, 5 Drawing Sheets

ANALOG PREPROCESSOR FOR JAW TRACKING DEVICE

FIELD OF THE INVENTION

The present invention relates to dental diagnostic instruments and, in particular, to a jaw tracking device for providing information relating to movement of a patient's mandible.

BACKGROUND OF THE INVENTION

A jaw tracking device is a diagnostic dental instrument used for displaying and/or recording the movement of a patient's lower jaw or mandible. In a typical arrangement, a magnet is temporarily mounted beneath the lower lip of the patient. The jaw tracking device includes an array of magnetic sensors positioned on opposite sides of the patient's mandible. As the patient's mandible moves, the distance between the magnet and each of the sensors varies, and each sensor generates a corresponding electrical signal. The electrical signals from the sensors may be processed to produce data that indicates mandible movement in an anterior/posterior, lateral and/or vertical plane. Selected views of such data may be presented to an operator on the display screen of a monitor or oscilloscope. Typically, a jaw tracking device can also generate a waveform indicative of the vertical velocity of the mandible over time. A jaw tracking device can easily and quickly provide the kind of factual information needed to determine and diagnose an occlusal problem.

Although jaw tracking devices have been used with great success for many years, there are difficulties inherent with the use of magnetic sensors to track mandible movement. In particular, the position of the patient's mandible is measured by taking the differential output of pairs of sensors located on opposite sides of the magnet along a selected axis. The resulting low level, analog signals are very sensitive to errors.

SUMMARY OF THE INVENTION

The present invention provides an improved analog preprocessor for a jaw tracking device. The jaw tracking device includes a plurality of magnetic sensors, each adapted to produce a first analog signal corresponding to the position of the sensor with respect to a magnet that is fixed in position with respect to a patient's mandible. The jaw tracking device also includes means for positioning the magnetic sensors on opposite sides of a patient's mandible, and means for receiving movement signals representing movement of the patient's mandible and providing movement information to an operator. The improved preprocessor processes the first analog signals to provide the movement signals. The preprocessor includes analog means for electrically combining the first analog signals to produce at least one analog position signal corresponding to the position of the magnet along a selected axis. The preprocessor further includes gain selection means responsive to operator input for providing a gain select signal, and a variable slope ramp generator that generates a ramp signal having a slope corresponding to the gain select signal. The position signal and ramp signal are input to a comparator that produces an output pulse having a length corresponding to the magnitude of the position signal. The output pulse is then converted into an analog movement signal having a magnitude corresponding to the pulse length.

DETAILED DESCRIPTION OF THE INVENTION

Figure 1:
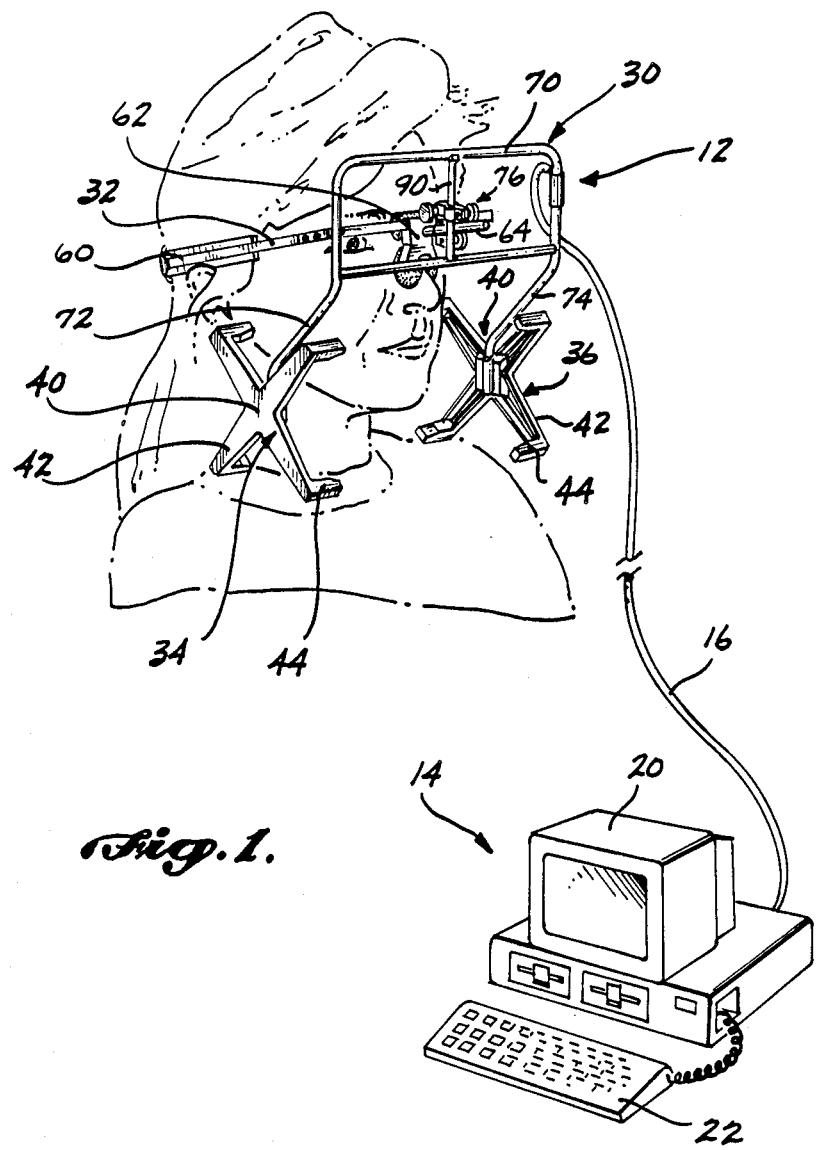
FIG. 1 is a perspective view of a jaw tracking device with which the analog preprocessor of the present invention may be used.

FIG. 1 illustrates a jaw tracking device in which the improved analog preprocessor of the present invention may be used. The jaw tracking device includes headpiece 12 mounted on the patient's head, and operator console 14 coupled to the headpiece via cable 16. In the illustrated embodiment, console 14 comprises a microcomputer that includes monitor 20 and keyboard 22. In general, the console may comprise any suitable device, such as a computer or a processor in combination with an oscilloscope, for providing information relating to mandible movement.

Headpiece 12 comprises frame 30, mounting system 32 and identical sensor arrays 34 and 36. Mounting system 32 includes strap 60, fasteners 61 (only one fastener shown), nosepiece 62 and mounting pin 64. The fasteners are adjustably connected to one another, and pass around the patient's head for securing the frame to the patient. Nosepiece 62 is connected to strap 60, and rests on the patient's nose to support the principle weight of the headpiece. Mounting pin 64 extends in a forward direction from nosepiece 62, and comprises a cylindrical pin that comprises the single point of support of the frame. The frame includes vertical crosspiece 90 that is adjustably connected to mounting pin 64 by coupler 76.

Each sensor array comprises central hub area 40, four arms 42 extending outwardly from hub area 40, and magnetic sensors 44 located at the outer end of each arm, each sensor extending in an inward direction from the outer end of the arm towards the other sensor array. The arms are formed as pairs that extend in opposite directions from one another from the hub area. In the illustrated embodiment, there are a total of four arms and four sensors in each sensor array, and adjacent arms on a single sensor array are rotated 90 degrees with respect to one another.

Each magnetic sensor 44 preferably comprises a Hall effect sensor that has a sensing axis that is parallel to the elongated dimension of the sensor and normal to the plane in which arms 42 lie. Sensor arrays 34 and 36 are mounted to frame 30 such that the sensor arrays are bilaterally symmetric with respect to the patient's mandible. In particular, each magnetic sensor 44 is positioned directly across from an identical sensor on the opposite side of the patient's mandible.

Figure 2:
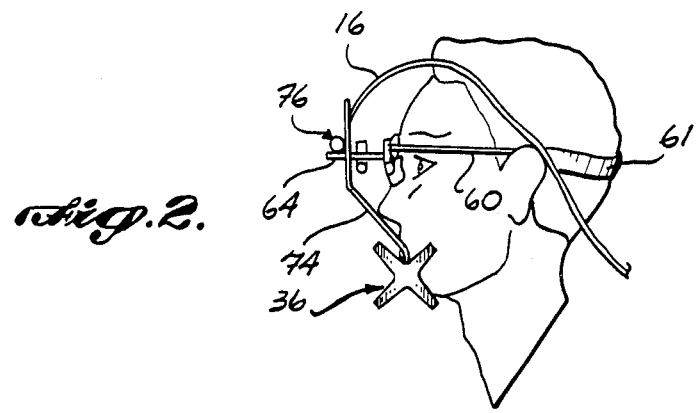
FIG. 2 is a side elevational view of the headpiece in use on a patient.
Figure 3:
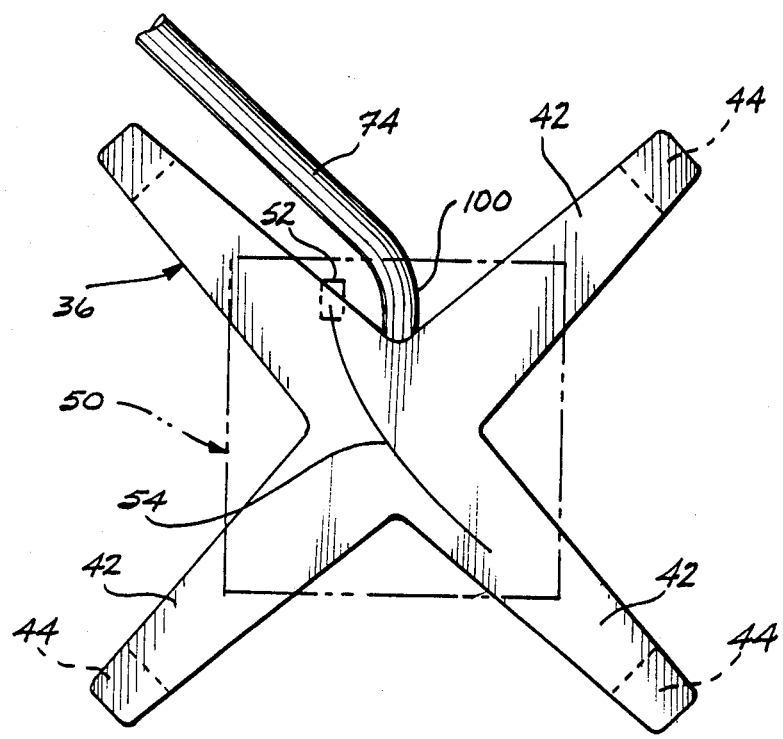
FIG. 3 is a side elevational view of one of the sensor arrays showing the detection zone.

Referring now to FIGS. 2 and 3, the eight sensors 44 operate to define a detection zone 50 that has a square cross section (as shown) and that occupies a volume that is centered between sensor arrays 34 and 36. The detection zone is the space in which there is a substantially linear relationship between the signals derivable from the sensor signals and the position of a magnet in the detection zone. To operate the jaw tracking device, a small magnet 52 is temporarily mounted beneath the lower lip of the patient. A principle function of headpiece 12 is to position sensor arrays 34 and 36 such that when the patient's lower jaw is raised (mouth closed), magnet 52 is positioned approximately as shown in FIG. 3 with respect to detection zone 50. Thereafter, movement of the patient's jaw will typically cause magnet 52 to follow a path such as path 54 shown in FIG. 3, and path 54 will remain within detection zone 50 throughout the range of mandible movement. The entire range of movement of the patient's mandible can thereby be accurately monitored by means of the jaw tracking device.

Figure 4:
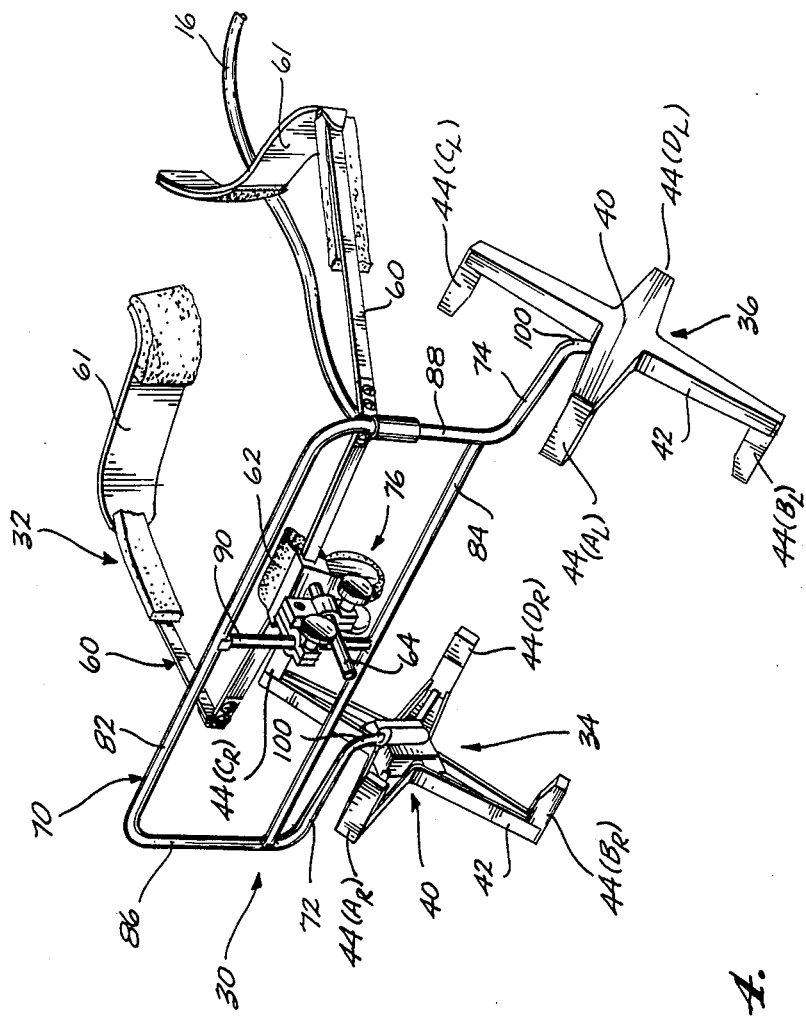
FIG. 4 is a perspective view of the headpiece.
Figure 5:
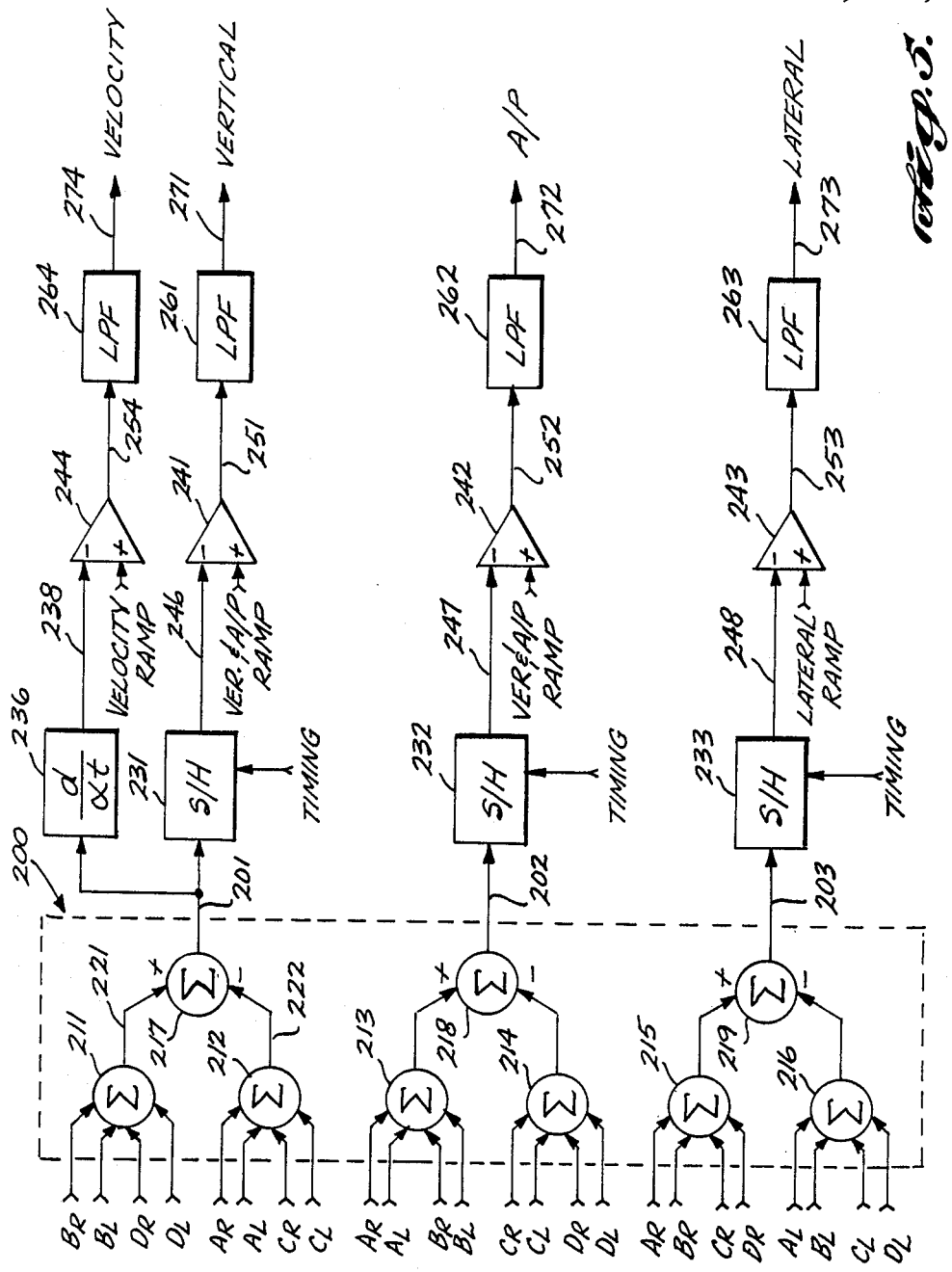
FIG. 5 is a block diagram of the analog preprocessor.
Figure 6:
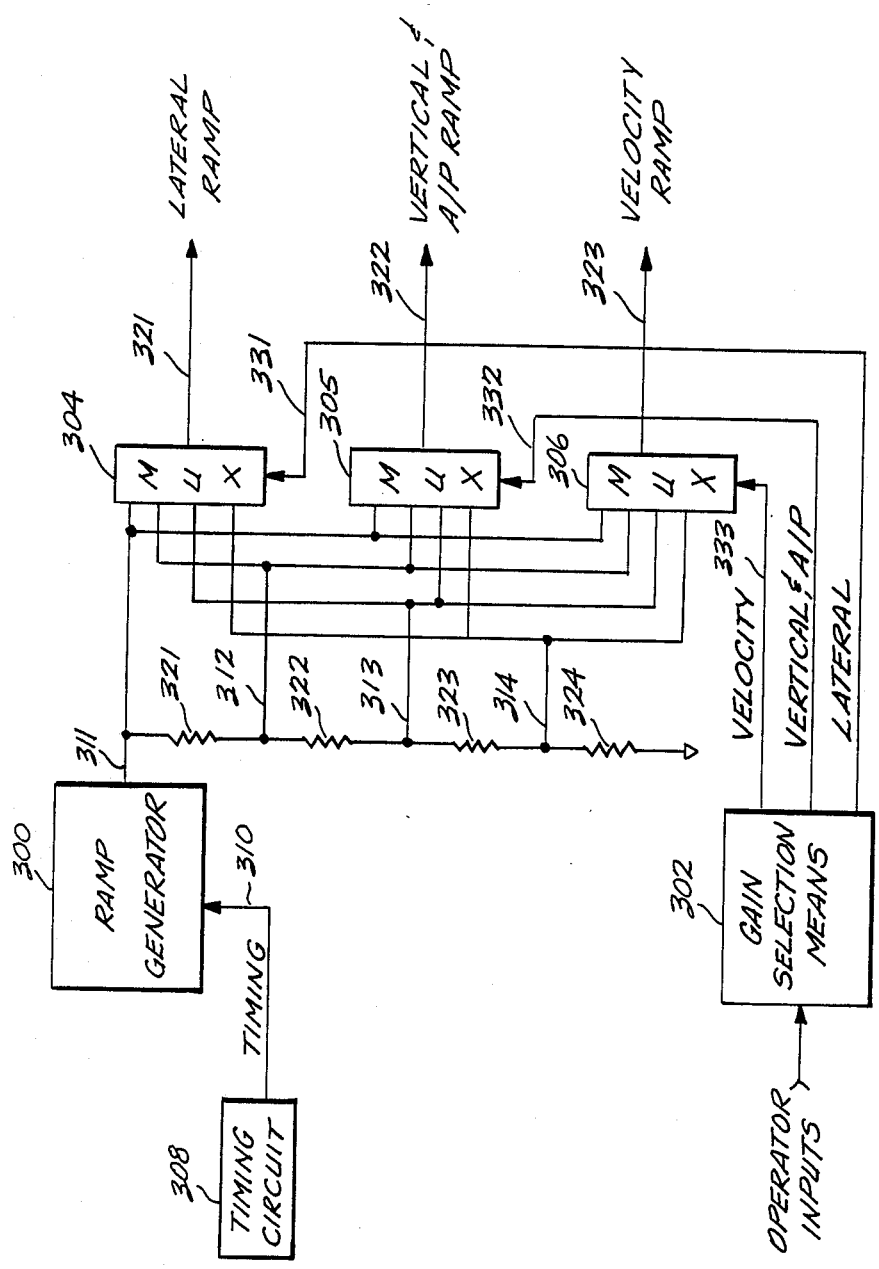
FIG. 6 is a block diagram of the variable slop ramp generator.

The analog preprocessor of the present invention is illustrated in FIGS. 5 and 6. However, referring initially to FIG. 4, the four sensors that are positioned to the left of the patient's mandible when the jaw tracking device is in use are designated $A_L$, $B_L$, $C_L$, and $D_L$, while the corresponding sensors that are positioned to the right of the patient's mandible are designated $A_R$, $B_R$, $C_R$, and $D_R$. In FIG. 5, these same designations are used to refer to the electrical signals produced by each of the respective sensors. These signals are input to combining circuit 200 that combines the eight sensor signals to produce a vertical position signal on line 201, an anterior/posterior (A/P) signal on line 202, and a lateral signal on line 203. Combining circuit 200 comprises summing junctions 211-219 that process the sensor signal according to the logic diagrammed in FIG. 5. For example, the vertical signal on line 201 is derived by first summing the magnitudes of the signals $B_R$, $B_L$, $D_R$, and $D_L$ to produce a first sum signal on line 221, by summing the signals $A_R$, $A_L$, $C_R$, and $C_L$ to produce a second sum signal on line 222, and then subtracting the second sum signal from the first sum signal to produce the vertical signal on line 201. Referring to FIG. 4, it can be seen that the operation performed by summing junctions 211, 212, and 217 is to subtract the signals from the sensors above a horizontal plane passing through the hub areas from the signals from the sensors below such plane. In a similar manner, summing junctions 213, 214, and 218 subtract the signals from the sensors posterior with respect to a vertical plane passing through the hub areas from the signals from the sensors anterior of such vertical plane. Finally, summing junctions 215, 216 and 219 subtract the signals from the left hand sensors from the signals from the right hand sensors, to produce the lateral signal on line 203.

The signals on lines 201-203 are periodically sampled, once each sample period, by sample and hold circuits 231-233 respectively in response to a common timing signal, and the resulting analog sample signals are provided as one input of respective comparators 241-243 via lines 246-248 respectively. As described below, the inputs to the positive terminals of the comparators comprise positive going ramps. Initially, at the beginning of each ramp, the sample signals on lines 246-248 will exceed the ramp voltage, and thus the outputs of comparators 241-243 on lines 251-253 respectively will be low. However, at some point during each sample period, the ramp will exceed the sample signal, and the output of that comparator will go and remain high until the ramp is reset at the beginning of the next sample period. As a result, pulses will appear on lines 251-253, the length of the pulses being a function of the magnitude of the sample signals input to the comparators, and of the steepness of the respective ramp signals.

The pulse signals on lines 251-253 are input to low pass filters 261-263 respectively. The low pass filters average the pulse signals to produce output signals on lines 271-273 having magnitudes proportional to the lengths of the pulse signals on lines 251-253, respectively, or, equivalently, to the duty cycles of the pulse signals. The signals on lines 271-273 represent the vertical, A/P and lateral signals output by the analog preprocessor of the present invention. The signals may then be processed in a conventional manner to produce appropriate displays on monitor 20.

The vertical input signal on line 201 is also input to differentiator 236, and the output signal of the differentiator on line 238 forms the input to the negative terminal comparator 244. A velocity ramp signal is input to the positive terminal of comparator 244, and the comparator operates in a manner similar to comparators 241-243 to produce a pulse signal on line 254 that is input to low pass filter 264, to produce a vertical velocity signal on line 274.

FIG. 6 illustrates the circuitry used to permit an operator to control the sensitivity or gain of the analog preprocessor. The gain select circuit of FIG. 6 includes ramp generator 300, gain selection means 302, multiplexors 304-306, and timing circuit 308. Gain selection means 302 receives operator gain selection inputs, and produces corresponding lateral, vertical & A/P, and velocity gain select signals on lines 331-333, respectively. Ramp generator 300 operates in response to a timing signal provided on line 310 by timing circuit 308, the timing signal on line 310 being identical to the timing signals used to trigger sample and hold circuits 231-233 in FIG. 5. A suitable frequency for the timing signal is 5 kH$_z$. In response to each timing pulse on line 310, ramp generator 300 resets, and begins producing a new positive going ramp signal on line 311. The signal on line 311 is applied to a voltage divider comprising resistors 321-324. As a result, ramp signals having four different slopes are produced on respective lines 311-314. The signals on lines 311-314 are input to each of the three multiplexors 304-306. Multiplexor 304 selects one of the ramp signals on lines 311-314 for output as the lateral ramp signal on line 321. The selection by multiplexor 304 is made in accordance with the lateral gain select signal on line 331. In a similar manner, multiplexor 305 selects one of the ramp signals on lines 311-314 for output as the vertical & A/P ramp signal on line 322, in accordance with the vertical & A/P gain select signal on line 332. Finally, multiplexor 306 selects one of the ramp signals for output as the velocity ramp signal on line 323, in accordance with the velocity gain select signal on line 333. The three ramp signals on lines 321-323 are input to the respective comparators in FIG. 5, as previously described.

While the preferred embodiments of the invention have been illustrated and described, it is to be understood that variations will be apparent to those skilled in the art. Accordingly, the invention is not to be limited to the specific embodiments illustrated and described, and the true scope and spirit of the invention are to be determined by reference to the following claims.

The embodiments of the invention in which an exclusive property or privilege is claimed are defined as follows:

1. In a jaw tracking device having a plurality of magnetic sensors, each adapted to produce a first analog signal corresponding to the position of the sensor with respect to a magnet that is fixed with respect to a patient's mandible, means for positioning the magnetic sensors on opposite sides of the patient's mandible, and controller means for receiving movement signals representing movement of the patient's mandible and for providing movement information to an operator of the jaw tracking device, an improved preprocessor for processing the first analog signals, the improved preprocessor comprising:

analog means for electrically combining the first analog signals to produce at least one analog position signal corresponding to the position of the magnet along a selected axis;

gain selection means responsive to inputs from an operator of the jaw tracking device for providing a gain select signal;

a variable slope ramp generator including means for generating a ramp signal having a slope corresponding to the gain select signal;

comparator means for comparing the position signal to the ramp signal and for generating an output pulse having a length corresponding to the magnitude of the position signal; and means for receiving the output pulse and for producing an analog movement signal having a magnitude corresponding to the pulse length.

2. The improved preprocessor of claim 1, wherein the variable slope ramp generator comprises a voltage divider and a fixed slope ramp generator for applying a fixed slope ramp signal to the voltage divider.

3. The improved preprocessor of claim 2, wherein the variable slope ramp generator comprises at least one multiplexor having a plurality of input terminals and a gain select terminal, the input terminals being connected to the voltage divider, and the gain select terminal being connected to receive the gain select signal.

4. The improved preprocessor of claim 1, wherein the comparator means includes a sample and hold circuit connected to receive the position signal and operative to sample the position signal to produce a sample position signal that is input to one input terminal of the comparator.

5. The improved preprocessor of claim 4, further including means for generating a timing signal, the sample and hold circuit being responsive to the timing signal to sample the position signal, and the variable slope ramp generator being responsive to the timing signal for resetting the ramp signal.

* * * * *